United States Patent [19]

Berger et al.

[11] Patent Number: 4,469,789

[45] Date of Patent: Sep. 4, 1984

[54] AMINO ACID AND PEPTIDE ESTERS OF LEUKO-INDOANILINE COMPOUNDS AND COMPOSITIONS FOR THE DETECTION OF PROTEOLYTIC ENZYMES

[75] Inventors: Dieter Berger, Viernheim; Franz Braun, Rimbach; Günter Frey, Ellerstadt; Wolfgang-Reinhold Knappe, Buerstadt; Manfred Kuhr; Wolfgang Werner, both of Mannheim, all of Fed. Rep. of Germany

[73] Assignee: Boehringer Mannheim GmbH, Mannheim, Fed. Rep. of Germany

[21] Appl. No.: 229,205

[22] Filed: Jan. 28, 1981

[30] Foreign Application Priority Data

Feb. 16, 1980 [DE] Fed. Rep. of Germany ....... 3005845

[51] Int. Cl.$^3$ .......................... C12Q 1/38; C12Q 1/36
[52] U.S. Cl. ......................................... 435/23; 435/24
[58] Field of Search ...................... 435/13, 23, 24, 29, 435/34, 805, 810, 26, 28; 424/2, 8; 422/56; 23/230 B, 932; 252/408; 436/904 G, 3, 800, 903

[56] References Cited

U.S. PATENT DOCUMENTS

| 3,087,794 | 4/1963 | Free et al. ............................. 23/932 |
| 4,116,774 | 9/1978 | Miniato et al. ......................... 435/23 |
| 4,167,449 | 9/1979 | Gargiulo et al. ........................ 435/24 |
| 4,278,763 | 7/1981 | Berger et al. ......................... 252/408 |
| 4,299,917 | 11/1981 | Berger et al. ......................... 435/23 |

OTHER PUBLICATIONS

Corbett et al., "Benzoquinone Imines Part VII, The Mechanism and Kinetics of the Reaction of p-Benzoquinone Diimines with Monohydric Phenols and the Ultraviolet Infrared and Nuclear Magnetic Resonance Spectra of the Resulting Indoanilines", *J. Chem. Soc.* (B) (1970), pp. 1418–1427.

*Primary Examiner*—Blondel Hazel
*Attorney, Agent, or Firm*—Felfe & Lynch

[57] ABSTRACT

This invention relates to new amino acid and peptide esters of leuko-indoaniline compounds and to a process for their preparation. In additional aspect, the invention relates to compositions containing such compounds for the detection of proteolytic enzymes and to methods for detecting such enzymes.

13 Claims, No Drawings

AMINO ACID AND PEPTIDE ESTERS OF LEUKO-INDOANILINE COMPOUNDS AND COMPOSITIONS FOR THE DETECTION OF PROTEOLYTIC ENZYMES

This invention relates to new amino acid and peptide esters of leuko-indoaniline compounds and to a process for their preparation. In additional aspect, the invention relates to compositions containing such compounds for the detection of proteolytic enzymes and to methods for detecting such enzymes.

The detection of leukocytes in body fluids, especially in the urine, is extremely important in the diagnosis of diseases of kidney and of the urogenital tract.

Hitherto, this detection has been carried out by the laborious counting of the leukocytes in non-centrifuged urine or in urine sediment.

It is inherent in both methods that only intact leukocytes are detected. On the other hand, it is known that the rate of leukocyte lysis is subject to enormous variations, depending upon the urine medium; thus, for example, in strongly alkaline urines, the leukocyte half-lifetime can be only 60 minutes. The result is leukocyte counts that are too low or, when urine samples have been left to stand for a rather long time, even falsely negative findings.

Apart from lysis error, the quantitative microscopic determination of the leukocytes in non-centrifuged, homogenized urine in a counting chamber gives quite dependable values. However, in practice, this method is only rarely used, since it is laborious, tiring, and time-consuming, and requires the use of trained personnel.

The overwhelming majority of the leukocyte determinations in urine are carried out in a medical practice by the so-called viewing field method on the urine sediment. For this purpose, the material to be investigated (sediment) must first be obtained by centrifuging. In this process, however, other components of the urine are also concentrated, such as, for example, salts and epithelial cells, which can make the microscopic counting of the leukocytes considerably more difficult. The varying content of sediment, inhomogeneities of the sediment, as well as possible differing microscopic magnifications or differing optical equipment for the microscope results in the fact that reports of this type on the number of leukocytes per microscopic viewing field may be affected by errors of several hundred percent.

It was the object of the present invention, therefore, to provide a diagnostic agent with which leukocytes present in body fluids can be detected in a manner that is simple and easy to use, and as quickly and completely as possible.

Since leukocytes possess a broad-spectrum enzyme activity, an enzymatic reaction suggests itself as a detection principle for such a leukocyte test.

U.S. Pat. No. 3,087,794 has already described and claimed a leukocyte detection method which is carried out via the peroxidase activity present in the granular leukocytes (granulocytes). An absorbent carrier, impregnated with hydrogen peroxide and an organic indicator, for example, o-tolidine, indicates the presence of leukocytes by the formation of a colored oxidation product. Such a test, however, has serious disadvantages: for one thing, peroxidase reactions using o-tolidine quite generally have a considerable tendency to be disturbed by reducing substances in the urine, such as, for example, ascorbic acid. Furthermore, there are references in several places in the literature to the instability of leukocyte peroxidase in the urine medium, which gives rise to falsely negative findings (see L. Mettler, Med. Welt 23 (1972), 399). Even more serious is the unsatisfactory selectivity toward erythrocytes that can be expected.

For some years, detection methods that depend on the esterolytic activity of the enzymes present in the systems to be determined have their fixed place in histo- and cyctochemical enzymology (cf., for example A. G. E. Pearse, *Histochemistry: Theoretical and Applied,* 3rd Ed. (Edinburgh/London/New York: Churchill Livingstone, 1968)). In principle, colorless or faintly colored esters are used, which mostly break down, through enzymatic splitting, into a colorless acid component and into an also colorless alcohol or phenol component. The latter is then converted into colored products, in a reaction that follows the enzymatic saponification (for example, by coupling with diazonium salts or oxidative reactions).

Thus, for example, F. Schmalzl and H. Braunsteiner, in Klin. Wschr. 46 (1968):642, describe a specific cytochemical leukocyte esterase detection with naphthol-AS-D-chloroacetate as substrate and a diazonium salt for the formation of a colored azo-compound.

As an agent for the quick and simple detection of leukocytes, for example in urine, two-component systems of this type have not proved suitable, since as is known, many compounds occurring in urine, such as, urobilinogen, stercobilinogen, bilirubin, and others, react with diazonium salts. Furthermore, this detection method is much too insensitive. For example, samples containing 5,000 leukocytes/μl do not show any reaction.

Surprisingly, it was now found that stable agents, which quickly produce an indication, and with which leukocytes can easily be detected in body fluids, are obtained when amino acid esters or peptide esters of leuko-indoanilines are used as a substrate for the detection of the esterases (proteases) present in the neutrophilic leukocyte granulocytes.

The subject of the present invention, therefore, is new amino acid and peptide esters of leuko-indoanilines of the general formula I

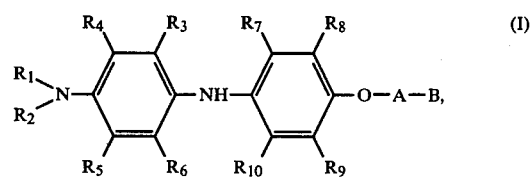

in which $R_1$, $R_2$, which may be the same or different, are hydrogen, a lower alkyl or a hydroxy-lower alkyl group or, together, an alkylene or alkylene-oxy-alkylene chain, $R_3$, $R_4$, $R_5$, $R_6$, which may be the same or different, are hydrogen or a halogen, a lower alkyl group, if necessary completely halogen substituted, a lower alkoxy, an aralkoxy, a hydroxy or a nitro group, $R_7$, $R_8$, $R_9$, $R_{10}$, which may be the same or different, are hydrogen or a halogen, a lower alkyl group, if necessary completely halogen substituted, a lower alkoxy, an aralkoxy, a lower acylamino, an acylalkenyl, a hydroxy, a lower alkylmercapto, a lower alkylsulfonyl, a carboxy, or a carbonyl group which, if necessary, is substituted by a lower alkoxy, aralkoxy, amino or lower alkylamino group or, at times, two adjacent substituents may represent a saturated or unsaturated hydrocarbon chain, in which a member of the chain may be replaced by a nitrogen atom, A is an amino acid or a peptide radical, and B is a nitrogen protective group customary in peptide chemistry or derived from it, as well as processes for the preparation of these compounds and their use for the preparation of agents for the detection of proteolytic enzymes.

The preparation of the new amino acid and peptide esters from leuko-indoanilines of general formula I can take place according to methods that are themselves known from peptide chemistry.

Preferably, the corresponding leuko-indoaniline compounds of general formula II

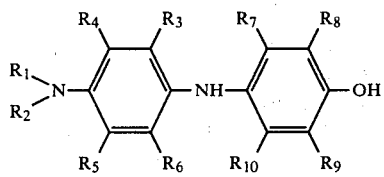
(II)

in which $R_1$, $R_2$, $R_3$, $R_4$, $R_5$, $R_6$, $R_7$, $R_8$, $R_9$, and $R_{10}$ have the meanings indicated above, are caused to react in a known manner with amino acids or peptides of the general formula III

HO—A—B          (III)

in which A and B have the meanings indicated above, or with appropriate reactive derivatives of them.

The acid chlorides or active esters are used as reactive derivatives.

The indoaniline compounds or the leuko-indoaniline substances of general formula II that are prepared from them by means of ordinary reducing agents (such as, for example, sodium sulfite or sodium dithionite) are known compounds; cf., for example, P. W. Vittum, G. H. Brown, *J. Amer. Chem. Soc.* 68 (1946): 2235 and *J. Amer. Chem. Soc.* 69 (1947): 152 and S Hünig, P. Richters, *Liebigs Ann.* 612 (1957): 282, or can be prepared analogously to known compounds. This is also true for amino acids and peptides of general formula III; cf., for example, Houben-Weyl, *Methoden der organischen Chemie*, Vol. 15/1/.

The subject of the present invention is, furthermore, an agent for the detection of proteolytic enzymes, especially for the detection of the proteases present in the leukocytes, consisting of an absorbent carrier, a film layer, a lyophilisate, a solution or a reagent tablet containing one or more chromogens, and a suitable buffering substance, as well as the customarily used adjuvants, if necessary, characterized in that amino acid and/or peptide esters of leuko-indoanilines of general formula I, indicated above, are used as chromogens.

The test principle of the agent according to the present invention is based on splitting the colorless amino acid and peptide esters of leuko-indoanilines of general formula I, which are claimed as chromogens, by means of esterases (proteases) into the practically colorless leuko-indoaniline compounds of general formula II, which are converted, in a secondary reaction, into the deep-blue colored indoanilines of general formula IIa, by means of atmospheric oxygen or an oxidizing agent.

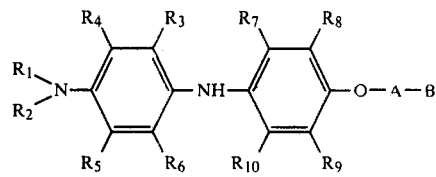
(I)

Esterases (Proteases)

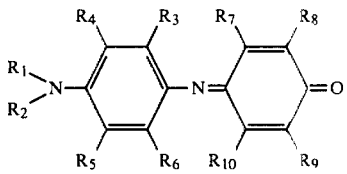
(II)

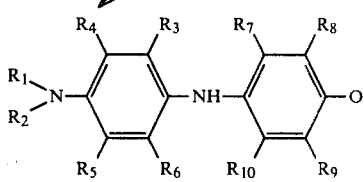
(IIa)

The substrates according to the present invention, as well as the agents prepared with them according to the present invention, are especially suited for the general detection of proteolytic enzymes, especially for the detection of the proteases present in the leukocytes. Other proteolytic enzymes, however, can also be detected with them, such as, for example, elastase, chymotrypsin or trypsin in purely aqueous solutions or also in body fluids, such as, for example, plasma, serum, liquor, pancreatic secretions, or aqueous stool extracts.

The lower alkyl radicals that appear in the definitions of $R_1$, $R_2$, $R_3$, $R_4$, $R_5$, $R_6$, $R_7$, $R_8$, $R_9$, and $R_{10}$ contain 1 to 6, preferably 1 to 4, carbon atoms, the methyl, ethyl, and n-butyl, as well as the methoxy, methylmercapto, and methylsulfonyl groups, being particularly preferred.

Hydrocarbon radicals with 1 to 6, preferably 2 to 5, carbon atoms, which may contain oxygen or nitrogen atoms as members of the chain, are to be understood under an "alkylene" and "alkylene oxyalkylene chain" in the definition of $R_1$ and $R_2$, as well as under a "saturated or unsaturated hydrocarbon chain" in the definition of $R_7$, $R_8$, $R_9$, and $R_{10}$. The butylene, pentylene, ethylene oxyethylene, butadienylene, and azabutadienylene radicals are especially preferred.

In the definition of $R_3$, $R_4$, $R_5$, $R_6$, $R_7$, $R_8$, $R_9$, and $R_{10}$, "halogen" means fluorine, chlorine, bromine, or iodine, preferably fluorine, chlorine, or bromine, bromine or fluorine being very especially preferred.

In the definition of $R_3$, $R_4$, $R_5$, $R_6$, $R_7$, $R_8$, $R_9$, and $R_{10}$, phenyl and naphthyl radicals substituted by lower alkoxy groups are in question as the aralkoxy group, the alkyl radical containing 1 to 5, preferably 1 to 3, carbon atoms. The benzoyl radical is especially preferred.

The amido groups of the lower aliphatic carboxylic acids with 1 to 5, preferably 1 to 3, carbon atoms, are to be understood under a "lower acylamino group" in the definition of $R_7$, $R_8$, $R_9$, and $R_{10}$. The acetylamino radical is especially preferred.

The "acylalkenyl group" in the definition of $R_7$, $R_8$, $R_9$, and $R_{10}$ means an alkenyl group substituted by radicals of aromatic carboxylic acids, such as, for example, the benzoic or naphthoic acids, the alkenyl group containing 2 to 5, preferably 2 to 3, carbon atoms. The benzoylvinyl radical is especially preferred.

The radicals of the natural α-amino acids in their L or D form, or even their racemic form, preferably come into question as the "amino acid radical" in the definition of A. Especially preferred are the radicals of glycine, alanine, valine, serine, leucine, methionine, phenylalanine, and tyrosine. Any hydroxyl group that may possibly be present can be protected in a familiar manner, preferably by means of an acetyl or benzyl radical.

In the definition of A, di-, tri-, tetra-, and pentapeptides, preferably di- and tripeptides, are to be understood under a "peptide radical," the amino acids mentioned above preferably being used as amino acid components.

Acyl, oxycarbonyl, and sulfonyl groups, for example, should be understood as a "nitrogen protective group customary in peptide chemistry" in the definition of B.

The amino acid and peptide esters of leuko-indoanilines of the general formula I, which are used as chromogens according to the present invention, are employed in concentrations of $10^{-4}$ 1 mol/liter, preferably $10^{-3}$ to $10^{-1}$ mol/liter of impregnating solution, coating mass, or liquid to be investigated.

An additional component of the diagnostic agent for the detection of proteolytic enzymes and, especially, of leukocyte proteases is a suitable buffer system. For this purpose, for example, a phosphate, borate, barbiturate, tris-(hydroxymethyl)aminomethane (=tris), 2-amino-2-methyl-propane-1,3 diol (=amediol) or amino acid buffer come under consideration. The pH value and capacity of the buffer are selected in such a way that a pH value of 6-10, and preferably of 7-9, appears in the measuring solution or on the test strip.

Furthermore, in the production of the agent according to the present invention for the detection of proteolytic enzymes, especially of leukocyte proteases in body fluids, oxidizing agents may be used in addition, in order to convert the leuko-indoaniline compounds of the general formula II, initially formed in the enzymatic reaction, into the deep-blue indoanilines of the general formula IIa.

These oxidizing agents, such as, for example, potassium hexacyanoferrate-III, potassium peroxodisulfate, potassium metaperiodate, sodium perborate, or potassium chromate are used in concentrations of $10^{-4}$ to $10^{-1}$ mol/liter preferably $10^{-3}$ to $10^{-2}$ mol/liter of impregnating solution coating mass, or fluid to be investigated.

An additional component of the agent for the detection of proteolytic enzymes according to the invention can be a wetting agent, since a more homogeneous color distribution and, in some cases, more brilliant colors can be achieved by means of this. Cation-active and also anion-active, as well as amphoteric and non-iogenic wetting agents may be used, in concentrations of 0.05-2% (w/v), preferably 0.1-1% (w/v).

In the production of the agent for the detection of proteolytic enzymes according to the present invention, furthermore, commonly used antioxidants (cf., for example, *Ullmanns Enzyklopädie der technischen Chemie*, Vol. 8), such as, for example, those of the phenol type, may be added, since, by so doing, the stability of the amino acid and peptide esters used according to the present invention is considerably improved with respect to oxidative decomposition processes. In the process, the antioxidants are used both as monocomponents and as synergistic systems (for example, hydroquinone plus hydroquinone monoalkyl ether). The antioxidants are used in concentrations of $10^{-4}$ to $10^{-2}$ mol/liter, and in so doing, the concentration should be selected in such a way that the oxidative secondary step to the colored indoanilines, which follows the enzymatic splitting of the amino acid esters into the leuko-indoaniline compounds, is not disturbed.

A phosphoric or phosphonic acid amide of general formula IV may serve as a stabilizer, as an additional component of the agent according to the present invention

in which $R_{11}$ means a dialkylamino, an alkoxy, an aryloxy, an alkyl, or an aryl group, or an N-morpholine radical, and $R_{12}$ and $R_{13}$ mean a dialkylamino group or an N-morpholine radical.

In the definition of $R_{11}$, hydrocarbon radicals with up to 10 carbon atoms come under consideration as the "alkoxy or alkyl group."

In the definition of $R_{11}$, phenyl or naphthyl radicals, if necessary substituted by halogen, lower alkyl, or alkoxy groups, should be understood under the definition of "aryl or aryloxy group."

An astonishing stabilization of the preparations is achieved with the aid of compounds of general formula IV.

Phosphoric and phosphonic acid amides of general formula IV are well known compounds. In German Pat. No. 2 235 127, for example, they are used as stabilizers of test strip preparations that operate on the basis of peroxidase detection.

The stabilizers of the phosphoric and phosphonic acid amide type of general formula IV are added to the aqueous impregnating solution in concentrations of 1-20% (w/v), preferably 5-15% (w/v).

Surprisingly, it was found that the reaction times of the diagnostic agent for the detection of proteolytic enzymes, especially of proteolytic leukocyte enzymes, according to the present invention, can be considerably shortened if one or more activators are used in addition to the previously mentioned chromogens and adjuvants. Suitable activators, for example, are (a) Alcohols of general formula V,

in which $R_{14}$ means hydrogen, a hydroxy or a lower alkoxy group, and K means a hydrocarbon radical;

(b) Metallic complexes of general formula VI,

in which
D means an alkali metal ion,

M a heavy metal ion,
m a whole number from 2 to 5,
n a whole number from 4 to 8, and
p 0 or 1.

The "lower alkoxy group" in the definition of $R_{14}$ contains 1 to 5, preferably 3 to 4, carbon atoms. The butyloxy group is especially preferred.

The hydrocarbon radical K in the definition of $R_{14}$ may be straight-chained or branched, saturated or unsaturated, cyclic or acylic, and contains 1 to 30, preferably 2 to 22, carbon atoms in the acyclic compounds, and 3 to 20, preferably 6 to 17, carbon atoms in the cyclic compounds.

In the activators of general formula VI, sodium and potassium ions preferably come under consideration as alkali metal ions D, and ions of the metals iron, nickel, chromium, manganese, cobalt, molybdenum, and vanadium preferably come under consideration as heavy metal ions M.

The following may be mentioned as examples of activators that can be used in the sense of the present invention:
1. 1-Hexanol
2. 1-Heptanol
3. 1-Octanol
4. 1-Nonanol
5. 1-Decanol
6. 1-Dodecanol
7. 1-Tetradecanol
8. 1-Pentadecanol
9. 1-Hexadecanol
10. 1-Heptadecanol
11. 1-Octadecanol
12. 1-Nonadecanol
13. 1-Eicosanol
14. 1-Docosanol
15. Cyclohexanol
16. 1-Cyclohexen-1-ol
17. Cycloheptanol
18. Cyclooctanol
19. Cyclononanol
20. Cyclodecanol
21. Cyclododecanol
22. Cycloheptadecanol
23. 9-Cycloheptadecen-1-ol
24. Citronellol
25. Geraniol
26. Nerol
27. Linalool
28. Farnesol
29. Nerolidol
30. cis-9-Octadecen-(1)-ol
31. Phytol
32. 1,5-Pentanediol
33. 1,6-Hexanediol
34. 1,7-Heptanediol
35. 1,8-Octanediol
36. 1,9-Nonanediol
37. 1,10-Decandiol
38. 1,12-Dodecandiol
39. 2-Butyloxyethanol
40. 2-(2-Butyloxyethyloxy)ethanol
41. Tripotassium hexacyanoferrate-III
42. Tetrapotassium hexacyanoferrate-II
43. Dipotassium tetracyanonickelate-II
44. Trisodium octacyanomolybdate-V
45. Disodium pentacyanonitrosylferrate-II
46. Tripotassium pentacyanonitrosylmanganate-I
47. Tripotassium pentacyanonitrosylchromate-I
48. Tripotassium pentacyanonitrosylcobaltate-I
49. Pentapotassium pentacyanonitrosylvanadate-I All the compounds used as activators according to the present invention are familiar.

The activators of general formula V are used in concentrations of 0.5–10%, preferably 1–5% (w/v), and the activators of general formula VI in concentrations of $10^{-4}$ to 1 mol/liter, preferably $10^{-3}$ to $10^{-1}$ mol/liter of impregnating solution.

For the production of the agent according to the present invention, for example, absorbent carriers, preferably filter paper, cellulose, or synthetic fiber fleeces, are impregnated with solutions of the necessary reagents usually used for the production of test strips (substrate, buffer, if necessary a wetting agent, an oxidizing agent, etc.) in readily volatile solvents, such as, for example, water, methanol, ethanol, or acetone. This is expediently done in two separate steps: First, impregnation is carried out with an aqueous solution containing the buffer and other water-soluble additives. After that, impregnation is carried out with a solution of the protease substrate of general formula I. In special cases, the impregnation sequence can also be reversed.

The finished test papers may be used as such, or stuck on to handles, in a familiar manner, or expediently sealed between plastics and fine-meshed networks according to Federal Republic of Germany Pat. No. 21 18 455.

For the production of film-coated test strips, all the reagents are introduced into a solution or dispersion of a film-forming substance, such as, for example, a polyvinyl ester or a polyamide, and homogeneously mixed. The mixture is spread in a thin layer on a plastic carrier and dried. After drying, the film-coated test strips according to the present invention are cut up, and may be used as such, or stuck on to handles, in a familiar manner, or, for example, sealed between plastics and fine-meshed networks according to Federal Republic of Germany Pat. No. 21 18 455.

The diagnostic agent, according to the present invention, for the detection of proteolytic enzymes, especially of leukocyte proteases, in the form of powder mixtures or reagent tablets, can be produced by treating and granulating the abovementioned components of the test with ordinary galenical additives. Additives of this kind are, for example, carbohydrates, such as, mono, oligo, or polysaccharides, or sugar alcohols, such as, mannitol, sorbitol, or xylitol, or other soluble inert compounds, such as polyethylene glycols or polyvinylpyrrolidone. In general, the powder mixtures or reagent tablets have a final weight of about 50–200 mg., preferably 50–80 mg.

For the production of lyophilizates, with a total weight, in each case, of about 5–20 mg, preferably of about 10 mg, a solution is freeze-dried which, along with all the reagents needed for the test, contains ordinary structure builders, such as, for example, polyvinylpyrrolidone, and possibly additional filling materials, such as, for example, mannitol, sorbitol, or xylitol.

The diagnostic agent according to the present invention, in the form of a solution, preferably contains all of the reagents needed for the test. As solvents, water or mixtures of water with a water-soluble organic solvent, such as, for example, methanol, ethanol, acetone, or dimethylformamide come under consideration. It may be advantageous, for reasons of storage stability, to divide the reagents needed for the test into two or more solutions which are not mixed together until the time of the actual investigation.

The diagnostic agents produced in this way make it possible, after dipping them into the body fluid to be investigated or after adding them to the body fluid in question, to detect, rapidly and simply, the presence of proteolytic enzymes by means of color formation, which can be evaluated visually or photometrically, for example, by reflectance photometry or in a cuvette. Since the activity of the leukocyte proteases per cell may be regarded as an essentially constant magnitude, the leukocyte concentration of the body fluid under investigation can be determined from the intensity of the color formation. At the same time, with the diagnostic agent according to the present invention, both intact and lyzed leukocytes are detected, since the activity of the leukocyte proteases is fully maintained even after the lysis of the leukocytes. Consequently, an error due to lysis does not occur.

EXAMPLE 1

4-[N-(toluene-4″-sulfonyl)-L-alanyloxy]-4′-dimethylamino-diphenylamine

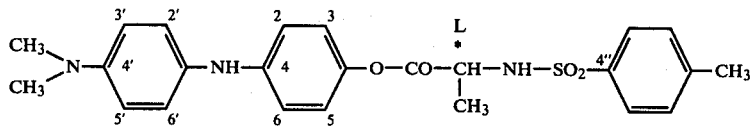

Solution 1

For the preparation of the acid chloride by the one-step method, 4.739 g (0.0195 mol) N-(toluene-4-sulfonyl)-L-alanine is dissolved in 35 ml of anhydrous dimethylformamide (DMF) and cooled to $-20°$ C. Then, while stirring and cooling, 1.645 ml (0.0195 mol) thionyl chloride is added with a pipette, and the reaction mixture is left to stand in a cold bath for 30 minutes at $-20°$ C.

Solution 2

A solution of 2.964 g (0.013 mol) 4-hydroxy-4′-dimethylaminodiphenylamine in 30 ml of anhydrous DMF is treated, in a protective gas atmosphere (nitrogen), with 1.79 ml (0.013 mol) triethylamine and 4.2 ml (0.052 mol) pyridine. The mixture is cooled to $-20°$ C.

Reaction

Solution 1 is poured into solution 2, and the reaction mixture stirred, with the exclusion of oxygen and water, for about 5 hours at $-20°$ C. After that, the mixture is gradually allowed to reach refrigerator temperature overnight.

To finish up, the reaction mixture is concentrated in a vacuum at a maximal bath temperature of 40°–50° C. The residue is taken up in about 100 ml of ethyl acetate, and washed three times with 50 ml of 5% sodium dicarbonate and in succession once with 50 ml of 5% citric acid. After drying the ethyl acetate phase over sodium sulfate, it is evaporated in a vacuum. The oily crude product thus obtained is purified by column chromatography, using silica gel and a 1:1 mixture of toluene and ethyl acetate. After distilling off the solvent from the collected fractions in a vacuum, the crystalline product is obtained by stirring the residue in ether. After filtering with suction, the residue is dissolved in very little methylene chloride, and precipitated with ether. In this way, 0.8 g (13.6%) 4-[N-(toluene-4″-sulfonyl)-L-alanyloxy]-4′-dimethylaminodiphenylamine is obtained in the form of colorless crystals, m.p. 149° C., $\alpha_D^{20} = -61.1°$, c=1% (acetone).

In an analogous manner, by the reaction of the appropriately substituted diphenylamine compounds (leuko-indoaniline) with the appropriate N-protected amino acids, the following substrates are obtained:

1.1: 2,6-dimethyl-4-[N-(toluene-4″-sulfonyl)-L-alanyloxy]-4′-dimethylaminodiphenylamine in the form of colorless crystals, m.p. 124°–126° C., $\alpha_D^{20} = -40.4°$, c=1% (acetone), 1.2: 3,5-dimethyl-4-[N-(toluene-4″-sulfonyl)-L-alanyloxy]-4′-dimethylaminodiphenylamine in the form of faintly grayish-blue crystals, m.p. 186°–189° C., TLC: commercially-prepared silica-gel plate, (elution agent: toluene-ethyl acetate 1:2, detection: UV, NH3 (gas), and potassium hexacyanoferrate-III, $R_F$-value: 0.53).

1.3: 4-[N-(toluene-4″-sulfonyl)-L-alanyloxy]-4′-diethylaminodiphenylamine, in the form of colorless crystals, m.p. 117°–120° C., $\alpha_D^{20} = -69.3°$, c=1% (acetone).

EXAMPLE 2

4-[N-(toluene-4″-sulfonyl)-L-alanyloxy]-4′-di-(n-butyl)-aminodiphenylamine

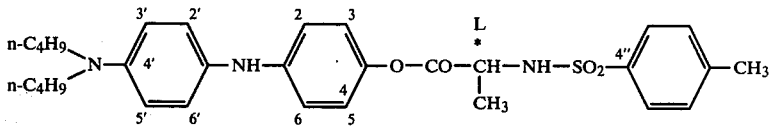

For the reaction by the active ester process, a mixture of 2.9 g (0.012 mol) N-(-toluene-4-sulfonyl)-L-alanine, 3.24 g (0.018 mol) N-hydroxybenzotriazole, and 2.59 g (0.012 mol) dicyclohexylcarbodiimide is first stirred in 60 ml of ethyl acetate for 2 hours at 0° C., and then for 2 hours at room temperature.

Then, with the exclusion of oxygen and water, there is added to the active ester formed in this way 2.49 g (0.008 mol) 4-hydroxy-4′-di-(n-butyl)-aminodiphenylamine and 1.1 ml (0.008 mol) triethylamine. The mixture is stirred at room temperature for about 15 hours. After filtering off with suction the N,N′-dicyclohexylurea formed the filtrate is worked up in the manner described in Example 1. The oily crude product is then purified by column chromatography on a silica gel with a mixture of toluene and ethyl acetate 4:1. After concentrating the solvent of the collected fractions, the remaining oily residue is rubbed with an ether-ligroin mixture. The product thus obtained is further purified by dissolving in little methylene chloride and precipitating with ligroin. In this way, 2.5 (58.5%) 4-[N-(toluene-4''-sulfonyl)-L-alanyloxy]-4'-di-(n-butyl)-aminodiphenylamine is obtained in the form of colorless crystals, m.p. 118° C., $\alpha_D° = 53.8°$, c=1% (acetone).

In an analogous manner, the following substrates are obtained by the reaction of the appropriately substituted diphenylamine compounds (leuko-indoanilines) with the appropriate N-protected amino acids:

2.1: 4-[N-(toluene-4''-sulfonyl)-L-analyloxy]-4'-aminodiphenylamine,
amorphous powder; $\alpha_D^{20} = -66.0°$, c=1% (acetone),
TLC: ready-made silica gel plate (elution agent: toluene-ethyl acetate 1:1, detection: UV, NH$_3$ (gas), and potassium hexacyanoferrate-III, R$_F$ value: 0.43)

2.2: 4-[N-(toluene-4''-sulfonyl)-L-alanyloxy]-4'-methylaminodiphenylamine,
amorphous powder; $\alpha_D^{20} = -62.3°$, c=1% (acetone),
TLC: ready-made silica gel plate (elution agent: heptane-acetone 2:1, detection: UV, NH$_3$ (gas), and potassium hexacyanoferrate-III, R$_F$ value: 0.38)

2.3: 4-[N-(toluene-4''-sulfonyl)-L-alanyloxy]-4'-(2'''-hydroxyethyl)ethylaminodiphenylamine 2.4: 4-[N-(toluene-4''-sulfonyl)-L-alanyloxy]-4'-(N-pyrrolidinyl)diphenylamine, colorless crystals; m.p. 139° C.; $\alpha_D^{20} = -58.9°$, c=1% (acetone)

2.5: 4-[N-toluene-4''-sulfonyl)-L-alanyloxy]-4'-(N-piperidinyl)diphenylamine,
amorphous powder; $\alpha_D^{20} = -73.4°$, c=1% (acetone),
TLC: ready-made silica gel plate (elution agent: heptane-ethyl acetate 3:2, detection: UV, NH$_3$ (gas), and potassium hexacyanoferrate-III, R$_F$ value: 0.20)

2.6: 4-[N-(toluene-4''-sulfonyl)-L-alanyloxy]-4'-(N-morpholinyl)diphenylamine, colorless crystals; m.p. 118° C.; $\alpha_D^{20} = -56.1$, c=1% (acetone)

2.7: 4-[N-(toluene-4''-sulfonyl)-L-alanyloxy]-2'-bromo-4'-dimethylaminodiphenylamine, colorless crystals; m.p. 107° C.; $\alpha_D^{20} = -54.3°$, c=1% (acetone)

2.8: 4-[N-(toluene-4''-sulfonyl)-L-alanyloxy]-2'-methyl-4'-dimethylaminodiphenylamine,
faintly grayish-blue crystals, m.p. 106° C.,
TLC: ready-made silica gel plate (elution agent: chloroform: methanol 99:1, detection: UV, NH$_3$ (gas), and potassium hexacyanoferrate-III, R$_F$ value: 0.26)

2.9: 4-[N-(toluene-4''-sulfonyl)-L-alanyl]-2'-trifluoromethyl-4'-dimethylaminodiphenylamine, colorless crystals, m.p. 109° C.; $\alpha_D^{20} = -50.1°$, c=1% (acetone)

2.10: 4-[N-toluene-4''-sulfonyl)-L-alanyloxy]-3'-trifluoromethyl-4'-dimethylaminodiphenylamine 2.11: 4-[N-(toluene-4''-sulfonyl)-L-alanyloxy]-2'5'-dimethoxy-4'-dimethylaminodiphenylamine 2.12: 4-[N-(toluene-4''-sulfonyl)-L-alanyloxy]-2'-benzyloxy-4'-dimethylaminodiphenylamine,
faint grayish-blue, viscous oil,
TLC: ready-made plate, silica gel (elution agent: toluene-ethyl acetate 1:1, detection: UV, NH$_3$ (gas), and potassium hexacyanoferrate-III, R$_F$ value: 0.64)

2.13: 4-[N-(toluene-4''-sulfonyl)-L-alanyloxy]-2'-hydroxy-4'-dimethylaminodiphenylamine
faintly gray crystals, m.p. 134° C.,
TLC: ready-made plate, silica gel (elution agent: toluene-ethyl acetate 4:1, detection: UV, NH$_3$ (gas), and potassium hexacyanoferrate-III, R$_F$ value: 0.49)

2.14: 4-[N-(toluene-4''-sulfonyl)-L-alanyloxy]-2'-nitro-4'-dimethylaminodiphenylamine,
faintly reddish, amorphous powder,
TLC: ready-made plate, silica gel (elution agent: chloroformmethanol 98:2, detection UV, NH$_3$ (gas), and potassium hexacyanoferrate-III, R$_F$ value: 0.50)

2.15: 2-methyl-4-[N-(toluene-4''-sulfonyl)-L-alanyloxy]-4'-dimethylaminodiphenylamine, colorless crystals, m.p. 134° C.; $\alpha_D^{20} = -5.8°$, c=1% (acetone)

2.16: 3-bromo-4-[N-(toluene-4''-sulfonyl)-L-alanyloxy]-4'-dimethylaminodiphenylamine, colorless crystals, m.p. 124° C.; $\alpha_D^{20} = -46.6°$, c=1% (acetone)

2.17: 3-methyl-4-[N-(toluene-4''-sulfonyl)-L-alanyloxy]-4'-dimethylaminodiphenylamine
faintly grayish-blue crystals, m.p. 97° C.,
TLC: ready-made plate, silica gel (elution agent: toluene-ethyl acetate 1:2, detection: UV, NH$_3$ (gas), and potassium hexacyanoferrate-III, R$_F$ value: 0.13)

2.18: 3-methyl-4-[N-(toluene-4''-sulfonyl)-L-alanyloxy[-4'-diethylaminodiphenylamine, colorless crystals, m.p. 79° C.; $\alpha_D^{20} = -67.7°$, c=1% (acetone)

2.19: 2,5-dimethyl-4-[N-(toluene-4''-sulfonyl)-L-alanyloxy]-4'-dimethylaminodiphenylamine, colorless crystals, m.p. 149° C.; $\alpha_D^{20} = -51.5°$, c=1% (acetone)

2.20: 2-trifluoromethyl-4-[N-(toluene-4''-sulfonyl)-L-alanyloxy]-4'-dimethylaminodiphenylamine,
yellowish, viscous oil; $\alpha_D^{20} = -28.1°$, c=1% (acetone)
TLC: ready-made plate, silica gel (elution agent: toluene-ethyl acetate 2:1, detection: UV, NH$_3$ (gas), and potassium hexacyanoferrate-III, R$_F$ value: 0.62)

2.21: 2-methoxy-4-[N-(toluene-4''-sulfonyl)-L-alanyloxy]-4'-dimethylaminodiphenylamine, colorless crystals, m.p. 73° C.; $\alpha_D^{20} = -58.0°$, c=1% (acetone)

2.22: 3-methoxy-4-[N-(toluene-4''-sulfonyl)-L-alanyloxy]-4'-dimethylaminodiphenylamine, colorless crystals, m.p. 130° C.; $\alpha_D^{20} = -40.0°$, c=1% (acetone)

2.23: 2,6-dimethoxy-4-[N-(toluene-4''-sulfonyl)-L-alanyloxy]-4'-dimethylaminodiphenylamine, colorless crystals, m.p. 127° C.; $\alpha_D^{20} = -50.1°$, c=1% (acetone)

2.24: 2-benzyloxy-4-[N-(toluene-4''-sulfonyl)-L-alanyloxy]-4'-dimethylaminodiphenylamine,
faintly grayish-blue crystals, m.p. 131° C.,
TLC: ready-made plate, silica gel (elution agent: toluene-ethyl acetate 2:1, detection: UV, NH$_3$ (gas), and potassium hexacyanoferrate-III, R$_F$ value: 0.60)

2.25: 2-hydroxy-4-[N-(toluene-4''-sulfonyl)-L-alanyloxy]-4'-dimethylaminodiphenylamine,
faintly grayish-blue crystals, m.p. 97° C.,
TLC: ready-made plate, silica gel (elution agent: toluene-ethyl acetate 1:1, detection: UV, NH$_3$ (gas), and potassium hexacyanoferrate-III, R$_F$ value: 0.46)

2.26: 3-acetylamino-4-[N-(toluene-4''-sulfonyl)-L-alanyloxy]-4'-dimethylaminodiphenylamine,
faintly gray crystals, m.p. 145°-148° C.,
TLC: ready-made plate, silica gel (elution agent: toluene-ethyl acetate 1:2, detection: UV, NH$_3$ (gas), and potassium hexacyanoferrate-III, $R_F$ value: 0.45)

2.27: 3-(benzoyl-vinyl)-4-(toluene-4''-sulfonyl)-L-alanyloxy]-4'-dimethylamino-diphenylamine, yellowish crystals, m.p. 146° C.; $\alpha_D^{20} = -77.7°$, c=1% (acetone)

2.28: N-(4'-diethylaminophenyl)-8-[N-(toluene-4''-sulfonyl-L-alanyloxy]-chinolyl-5-amine,
faintly grayish-blue crystals, m.p. 164°–166° C.,
TLC: ready-made plate, silica gel (elution agent: toluene-ethyl acetate 1:1, detection: UV, NH₃ (gas), and potassium hexacyanoferrate-III, $R_F$ value: 0.28)

2.29: N-(4'-dimethylaminophenyl)-4-[N-(toluene-4''-sulfonyl)-L-alanyloxy]-naphthyl-1-amine, faintly grayish-blue, amorphous powder, m.p. from 70° C.,
TLC: ready-made plate, silica gel (elution agent: toluene-ethyl acetate 2:1, detection: UV, NH₃ (gas), and potassium hexacyanoferrate-II, $R_F$ value: 0.45)

2.30: N-(4'-dimethylaminophenyl)-3-chloro-4-[N-(toluene-4''-sulfonyl)-L-alanyloxy]-naphthyl-1-amine, amorphous powder,
TLC: ready-made plate, silica gel (elution agent: toluene-ethyl acetate 1:1, detection: UV, NH₃ (gas), and potassium hexacyanoferrate-III, $R_F$ value: 0.67)

2.31: N-(4'-dimethylaminophenyl)-3-carboxy-4-[N-(toluene-4''-sulfonyl)-L-alanyloxy]-naphthyl-1-amine, faintly grayish-blue crystals, m.p. 104°–106° C.,
TLC: ready-made plate, silica gel (elution agent: xylene-methylethylketone 1:1 with 1% glacial acetic acid, detection: UV, NH₃ (gas), and potassium hexacyanoferrate-III, $R_F$ value: 0.20)

2.32: N-(4'-dimethylaminophenyl)-3-benzyloxycarbonyl-4-[N-(toluene-4''-sulfonyl)-L-alanyloxy]-naphthyl-1-amine, colorless crystals, m.p. 141° C.; $\alpha_D^{20} = -55.6°$, c=1% (acetone)

2.33: N-(4'-dimethylaminophenyl)-3-carbamoyl-4-[N-(toluene-4''-sulfonyl)-L-alanyloxy]-naphthyl-1-amine 2.34: N-(4'-dimethylaminophenyl)-3-(n-butyl-carbamoyl)-4-[N-(toluene-4''-sulfonyl)-L-alanyloxy]-naphthyl-1-amine 2.35: 4-[N-(toluene-4''-sulfonyl)-glycyloxy]-4'-dimethylaminodiphenylamine, colorless crystals, m.p. 126° C.

2.36: 4-[N-(toluene-4''-sulfonyl)-D-alanyloxy]-4'-dimethylaminodiphenylamine, faintly grayish-blue crystals, m.p. 142° C.,
TLC: ready-made plate, silica gel (elution agent: chloroformmethanol 98:2, detection: UV, NH₃ (gas), and potassium hexacyanoferrate-III, $R_F$ value: 0.31)

2.37: 4-[N-(toluene-4''-sulfonyl)-L-seryloxy]-4'-dimethylaminodiphenylamine, colorless crystals, m.p. 141° C.; $\alpha_D^{20} = -45.6°$, c=1% (acetone)

2.38: 4-[N-(toluene-4''-sulfonyl)-L-valyloxy]-4'-dimethylaminodiphenylamine, colorless crystals, m.p. 131° C.; $\alpha_D^{20} = -46.9°$, c=1% (acetone)

2.39: 2-methoxy-4-[N-(toluene-4''-sulfonyl)-L-valyloxy]-4'-dimethylaminodiphenylamine, colorless, amorphous powder; $\alpha_D^{20} = -44.2°$, c=1% (acetone),
TLC: ready-made plate, silica gel (elution agent: heptane-ethyl acetate 1:1, detection: UV, NH₃(gas), and potassium hexacyanoferrate-III, $R_F$ value: 0.44)

2.40: 2-methylmercapto-4-[N-(toluene-4''-sulfonyl)-L-valyloxy]-4'-dimethylaminodiphenylamine, faintly grayish-blue crystals, m.p. 94° C.,
TLC: ready-made plate, silica gel (elution agent: toluene-ethyl acetate 2:1, detection: UV, NH₃ (gas), and potassium hexacyanoferrate-III, $R_F$ value: 0.58)

2.41: 2-methylsulfonyl-4-[N-(toluene-4''-sulfonyl)-L-valyloxy]-4'-dimethylaminodiphenylamine 2.42: 4-[N-(toluene-4''-sulfonyl)-L-leucyloxy]-4'-dimethylaminodiphenylamine,
yellowish, viscous oil; $\alpha_D^{20} = -30.7°$, c=1% (acetone),
TLC: ready-made plate, silica gel (elution agent: toluene-ethyl acetate 1:2, detection: UV, NH₃ (gas), and potassium hexacyanoferrate-III, $R_F$ value: 0.66)

2.43: 4-[N-(toluene-4''-sulfonyl)-L-methionyloxy]-4'-dimethylaminodiphenylamine,
amorphous powder; $\alpha_D^{20} = -28.1°$, c=1% (acetone),
TLC: ready-made plate, silica gel (elution agent: toluene-dioxane 9:1, detection: UV, NH₃ (gas), and potassium hexacyanoferrate-III, $R_F$ value: 0.23)

2.44: 4-[N-(toluene-4''-sulfonyl)-L-phenylalanyloxy]-4'-dimethylaminodiphenylamine, colorless crystals, m.p. 125° C.; $\alpha_D^{20} = -8.5°$, c=1% (acetone)

2.45: 4-[N-(toluene-4''-sulfonyl)-O-benzyl-L-tyrosyloxy]-4'-dimethylaminodiphenylamine,
The resultant oily crude product was worked up further without purification.
By reductive splitting off of the benzyl radical, with the aid of a hydrogen/platinum catalyst, the following is obtained:

2.46: 4-[N-(toluene-4''-sulfonyl)-L-tyrosyloxy]-4'-dimethylaminodiphenylamine,
faintly grayish-blue crystals, m.p. 181°–183° C.,
TLC: ready-made plate, silica gel (elution agent: toluene-ethyl acetate 1:2, detection: UV, NH₃ (gas), and potassium hexacyanoferrate-III, $R_F$ value: 0.52)

2.47: 4-[N-(toluene-4''-sulfonyl)-L-alanyl-L-alanyloxy]-4'-dimethylaminodiphenylamine, colorless crystals, m.p. 155° C.; $\alpha_D^{20} = -46.0°$, c=1% (acetone)

2.48: 4-[N-(toluene-4''-sulfonyl)-D-alanyl-L-alanyloxy]-4'-dimethylaminodiphenylamine, colorless crystals, m.p. 127° C.; $\alpha_D^{20} = -28.8°$, c=1% (acetone)

2.49: 4-[N-(toluene-4''-sulfonyl)-L-alanyl-L-analyl-L-alanyloxy]-4'-dimethylaminodiphenylamine,
faintly grayish-blue crystals, m.p. 172° C.,
TLC: ready-made plate, silica gel (elution agent: heptane-ethyl acetate 1:8, detection: UV, NH₃ (gas), and potassium hexacyanoferrate-III, $R_F$ value: 0.25)

2.50: 4-(N-acetyl-L-alanyloxy)-4'-dimethylaminodiphenylamine, colorless crystals, m.p. 142° C.; $\alpha_D^{20} = -7.60$, c=1% (acetone)

2.51: 4-(N-benzoyl-D,L-alanyloxy)-4'-dimethylaminodiphenylamine, colorless crystals, m.p. 143° C.

2.52: 4-[N-(tert-butyloxycarbonyl)-L-alanyloxy]-4'-dimethylaminodiphenylamine, colorless crystals, m.p. 128° C.; $\alpha_D^{20} = -44.8°$, c=1% (acetone)

2.53: 4-[N-(benzyloxycarbonyl)-L-alanyloxy]-4'-dimethylaminodiphenylamine, colorless crystals, m.p. 116°–117° C.; $\alpha_D^{20} = -34.4°$, c=1% (acetone).

EXAMPLE 3

Filter paper (for example, Schleicher & Schüll 23 SL) is successively impregnated with the following solutions, and then dried at 60° C.:

Solution 1

| disodium tetraborate decahydrate | 1.91 g |
| --- | --- |
| distilled water about | 30 ml |

Adjust the solution with 0.1N hydrochloric acid to a pH value of 8.0
distilled water: to 100.0 ml.

Solution 2

| 4-[N—(toluene-4''-sulfonyl)-L-alanyloxy]-4'-dimethylaminodiphenylamine | 45.3 mg |
| --- | --- |
| acetone to | 100.0 ml |

A colorless test paper is obtained which, when dipped into leukocyte-containing urines, turns light to dark blue, depending upon the leukocyte concentration. The following can be established:
5,000 leukocytes/μl of urine in about 2 minutes
1,000 leukocytes/μl of urine in about 5 minutes
500 leukocytes/μl of urine in about 8 minutes
200 leukocytes/μl of urine in about 12 minutes The sensitivity of the test lies at about 200 leukocytes/μl. The evaluation can also be carried out by remission photometry between 570 and 720 nm.

Test papers with similar properties (sensitivities: 200–2,000 leukocytes/μl) are obtained, if instead of 4-[N-(toluene-4''-sulfonyl)-L-alanyloxy]-4'-dimethylamino-4'-diphenylamine, the following substrates are used. In so doing—unless otherwise mentioned—light to dark blue colorations of the otherwise colorless or almost colorless test papers are observed upon dipping them into leukocyte-containing urines.

3.1: 4[N-(toluene-4''-sulfonyl)-L-alanyloxy]-4'-aminodiphenylamine
3.2: 4-[N-(toluene-4''-sulfonyl-L-alanyloxy]-4'-methylaminodiphenylamine
3.3: 4-[N-(toluene-4''-sulfonyl)-D-alanyloxy]-4'-dimethylaminodiphenylamine
3.4: 4-[N-(toluene-4''-sulfonyl)-L-alanyloxy]-4'-dimethylaminodiphenylamine hydrochloride
3.5: 4-[N-(toluene-4''-sulfonyl)-L-alanyloxy]-4'-diethylaminodiphenylamine
3.6: 4-[N-(toluene-4''-sulfonyl)-L-alanyloxy]-4'-(2'''-hydroxyethyl)-ethylaminodiphenylamine
3.7: 4-[N-(toluene-4''-sulfonyl)-L-alanyloxy]-4'-(N-pyrrolidinyl)diphenylamine
3.8: 4-[N-(toluene-4''-sulfonyl)-L-alanyloxy]-4'-(N-piperidinyl)diphenylamine
3.9: 4-[N-(toluene-4''-sulfonyl)-L-alanyloxy]-4'-(N-morpholinyl)diphenylamine
3.10: 4-[N-(toluene-4''-sulfonyl)-L-alanyloxy]-4'-dibutylaminodiphenylamine
3.11: 3-acetylamino-4-[N-(toluene-4''-sulfonyl)-L-alanyloxy]-4'-dimethylaminodiphenylamine
3.12: 3-(benzoylvinyl)-4-[N-(toluene-4''-sulfonyl)-L-alanyloxy]-4'-dimethylaminodiphenylamine
3.13: 2-benzyloxy-4-[N-(toluene-4''-sulfonyl)-L-alanyloxy]-4'-dimethylaminodiphenylamine
3.14: 3-bromo-4-[N-(toluene-4''-sulfonyl)-L-alanyloxy]-4'-dimethylaminodiphenylamine
3.15: 2-hydroxy-4-[N-(toluene-4''-sulfonyl)-L-alanyloxy]-4'-dimethylaminodiphenylamine
3.16: 2-methoxy-4-[N-(toluene-4''-sulfonyl)-L-alanyloxy]-4'-dimethylaminodiphenylamine
3.17: 3-methoxy-4-[N-(toluene-4''-sulfonyl)-L-alanyloxy]-4'-dimethylaminodiphenylamine
3.18: 2,6-dimethoxy-4-[N-(toluene-4''-sulfonyl)-L-alanyloxy]-4'-dimethylaminodiphenylamine
3.19: 2-methyl-4-[N-(toluene-4''-sulfonyl)-L-alanyloxy]-4'-dimethylaminodiphenylamine
3.20: 3-methyl-4-[N-(toluene-4''-sulfonyl)-L-alanyloxy]-4'-dimethylaminodiphenylamine
3.21: 3-methyl-4-[N-(toluene-4''-sulfonyl)-L-alanyloxy]-4'-dimethylaminodiphenylamine
3.21: 3-methyl-4-[N-(toluene-4''-sulfonyl)-L-alanyloxy]-4'-dimethylaminodiphenylamine
3.22: 2,5-dimethyl-4-[N-(toluene-4''-sulfonyl)-L-alanyloxy]-4'-dimethylaminodiphenylamine
3.23: 3,5-dimethyl-4-[N-(toluene-4''-sulfonyl)-L-alanyloxy]-4'-dimethylaminodiphenylamine
3.24: 2,6-dimethyl-4-[N-(toluene-4''-sulfonyl)-L-alanyloxy]-4'-dimethylaminodiphenylamine
3.25: 2-trifluoromethyl-4-[N-(toluene-4''-sulfonyl)-L-alanyloxy]-4'-dimethylaminodiphenylamine
3.26: 2'-benzyloxy-4-[N-(toluene-4''-sulfonyl)-L-alanyloxy]-4'-dimethylaminodiphenylamine
3.27: 2'-bromo-4-[N-(toluene-4''-sulfonyl)-L-alanyloxy]-4'-dimethylaminodiphenylamine
3.28: 2'-hydroxy-4-[N-(toluene-4''-sulfonyl-L-alanyloxy]-4'-dimethylaminodiphenylamine, Change of color from pink to blue.
3.29: 2',5'-dimethoxy-4-[N-(toluene-4''-sulfonyl)-L-alanyloxy]-4'-dimethylaminodiphenylamine
3.30: 2'-methyl-4-[N-(toluene-4''-sulfonyl)-L-alanyloxy]-4'-dimethylaminodiphenylamine
3.31: 2'-nitro-4-[N-(toluene-4''-sulfonyl)-L-alanyloxy]-4'-dimethylaminodiphenylamine, Change of color from red to blue.
3.32: 2'-trifluoromethyl-4-[N-(toluene-4''-sulfonyl)-L-alanyloxy]-4'-dimethylaminodiphenylamine
3.33: 3'-trifluoromethyl-4-[N-(toluene-4''-sulfonyl)-L-alanyloxy]-4'-dimethylaminodiphenylamine
3.34: 4-[N-(toluene-4''-sulfonyl)-L-alanyl-L-alanyloxy]-4'-dimethylaminodiphenylamine
3.35: 4-[N-(toluene-4''-sulfonyl)-D-alanyl-L-alanyloxy]-4'-dimethylaminodiphenylamine
3.36: 4-[N-(toluene-4''-sulfonyl)-L-alanyl-L-alanyl-L-alanyloxy]-4'-dimethylaminodiphenylamine
3.37: 4-(N-acetyl-L-alanyloxy)-4'-dimethylaminodiphenylamine
3.38: 4-(N-benzoyl-D,L-alanyloxy)-4'-dimethylaminodiphenylamine
3.39: 4-(N-benzyloxycarbonyl-L-alanyloxy)-4'-dimethylaminodiphenylamine
3.40: 4-[N-(tert-butyloxycarbonyl)-L-alanyloxy]-4'-dimethylaminodiphenylamine
3.41: 4-[N-(toluene-4''-sulfonyl)-glycyloxy]-4'-dimethylaminodiphenylamine
3.42: 4-[N-(toluene-4''-sulfonyl)-L-leucyloxy]-4'-dimethylaminodiphenylamine
3.43: 4-[N-(toluene-4''-sulfonyl)-L-methionyloxy]-4''-dimethylaminodiphenylamine
3.44: 4-[N-(toluene-4''-sulfonyl)-L-phenylalanyloxy]-4'-dimethylaminodiphenylamine
3.45: 4-[N-(toluene-4''-sulfonyl)-L-seryloxy]-4'-dimethylaminodiphenylamine 3.46: 4-[N-(toluene-4"-sulfonyl)-O-benzyl-L-tyrosyloxy]-4'-dimethylaminodiphenylamine
3.47: 4-[N-(toluene-4"-sulfonyl)-L-tyrosyloxy]-4'-dimethylaminodiphenylamine
3.48: 4-[N-(toluene-4"-sulfonyl)-L-valyloxy]-4'-dimethylaminodiphenylamine
3.49: 2-methylmercapto-4-[N-(toluene-4"-sulfonyl)-L-valyloxy]-4'-dimethylaminodiphenylamine
3.50: 2-methoxy-4-[N-(toluene-4"-sulfonyl)-L-valyloxy]-4'-dimethylaminodiphenylamine
3.51: 2-methylsulfo-4-[N-(toluene-4"-sulfonyl)-L-valyloxy]-4'-dimethylaminodiphenylamine
3.52: N-(4'-diethylaminophenyl)-8-[N-(toluene-4"-sulfonyl)-L-alanyloxy]-chinolyl-5-amine, Change of color from pale green to blue.
3.53: N-(4'-dimethylaminophenyl)-4-[N-(toluene-4"-sulfonyl)-L-alanyloxy]-naphthyl-1-amine
3.54: N-(4'-dimethylaminophenyl)-3-chloro-4-[N-(toluene-4"-sulfonyl)-L-alanyloxy]-naphthyl-1-amine
3.55: N-(4'-dimethylaminophenyl)-3-carboxy-4-[N-(toluene-4"-sulfonyl-L-alanyloxy]-naphthyl-1-amine
3.56: N-(4'-dimethylaminophenyl)-3-benzyloxycarbonyl-4-[N-(toluene-4"-sulfonyl)-L-alanyloxy]-naphthyl-1-amine
3.57: N-(4'-dimethylaminophenyl)-3-carbamoyl-4-[N-(toluene-4"-sulfonyl-L-alanyloxy)-naphthyl-1-amine
3.58: N-(4'-dimethylaminophenyl)-3-(n-butylcarbamoyl)-4-[N-(toluene-4"-sulfonyl)-L-alanyloxy]-naphthyl-1-amine

EXAMPLE 4

Filter paper (for example, Schleicher & Schüll 23 SL) is successively impregnated with the following solutions, and then dried at 60° C.

Solution 1

| tri-(hydroxymethyl)-aminomethane | 1.22 g |
| potassium hexacyanoferrate-III | 0.1645 g |
| distilled water about | 50 ml |

Adjust the solution with 1M hydrochloric acid to a pH value of 8.5.
distilled water: to 100 ml.

Solution 2

| 4-[N—(toluene-4"-sulfonyl)-L-valyloxy]-4'-dimethylaminodiphenylamine | 48.1 mg |
| acetone to | 100 ml |

A yellow test paper is obtained which, when dipped into leukocyte-containing urines, changes through green to blue.

The sensitivity of the test lies to about 300 leukocytes/µl of urine.

The evaluation can also be carried out by reflectance photometry between 570 and 720 nm.

With oxidizing agents, such as, for example, the potassium hexacyanoferrate-III used above, or with potassium peroxodisulfate, potassium metaperiodate, sodium perborate, and potassium chromate, test papers can be obtained with the other substrates of Examples 1 and 2 which, compared with analogous test papers without oxidizing agents, exhibit, to some extent, slightly shortened reaction times.

EXAMPLE 5

Filter paper (for example, Schleicher & Schüll 23 SL) is successively impregnated with the following solutions, and then dried at 60° C.

Solution 1

| disodium tetraborate decahydrate | 7.63 g |
| distilled water | 80 ml |
| N—(3-octanoylamidopropyl)-N,N—dimethyl-ammonioacetate | 0.5 g |

The solution is adjusted with 1M hydrochloric acid to a pH value of 8.0, and after cooling to 25° C. distilled water: to 100.0 ml.

Solution 2

| 3-bromo-4-[N—(toluene-4"-sulfonyl)-L-alanyloxy]-4'-dimethylaminodiphenylamine | 53.2 mg |
| acetone to | 100.0 ml |

A colorless test paper is obtained which, when dipped into leukocyte-containing urines, turns light to dark blue, according to the leukocyte concentration. Compared with the preparation of Example 3, there are somewhat shortened reaction times and slightly more brilliant colors.

With wetting agents, such as, for example, the one used above (amphoteric), but also, for example, with nonylphenolpolyglycol ether (non-ionogenic), or benzyltrimethylammonium chloride (cation-active), or sodiumsulfonatododecylbenzene (anion-active), test papers can be obtained with other substrates, too, of Examples 1 and 2 which, compared with analogous test papers without wetting agents, exhibit, to some extent, slightly shortened reaction times and somewhat more brilliant colors.

EXAMPLE 6

Filter paper (for example, Schleicher & Schüll 2316) is successively impregnated with the following solutions, and then dried at 60° C.

Solution 1

| disodium tetraborate decahydrate | 3.81 g |
| distilled water to | 80 ml |

The solution is adjusted with 1M hydrochloric acid to a pH value of 8.0.
distilled water: to 100.0 ml.

Solution 2

| 4-[N—(toluene-4"-sulfonyl)-L-alanyloxy]-4'-(N—pyrrolidinyl)-diphenylamine | 47.9 mg |
| tert-butylhydroquinone | 8.8 mg |
| 3-(tert-butyl)-4-hydroxyanisol | 9.0 mg |
| acetone | 100.0 ml |

A white test paper is obtained which, when dipped into leukocyte-containing urines, turns light to dark blue, according to the leukocyte concentration.

With the other substrates, too, of Examples 1 and 2, as well as with other antioxidants, such as methyl- and dimethylhydroquinone, 2,6-di-(tert-butyl)-4-methylphenol, 2,4,6-tri-(tert-butyl)-phenol, 4-methoxyphenol, or (2-methoxy-2-methyl-1-propyl)hydroquinone, white test papers are obtained which, in comparison to analogous test papers without antioxidants, do not show a blue discoloration even with rather long storage.

The slight delay of the color reaction upon dipping into leukocyte-containing urines may also be eliminated by also impregnating the oxidizing agents mentioned in Example 4.

EXAMPLE 7

Filter paper (for example, Schleicher & Schüll 23 SL) is successively impregnated with the following solutions, and then dried at 60° C.

Solution 1

| | |
|---|---|
| disodium tetraborate decahydrate | 7.63 g |
| distilled water about | 70 ml |
| phosphoric acid trimorpholide | 10.0 g |

The solution is adjusted with 1M hydrochloric acid to a pH value of 8.0, and after cooling to 25° C. distilled water: to 100 ml.

Solution 2

| | |
|---|---|
| 3-methyl-4-[N—(toluene-4"-sulfonyl)-L-alanyloxy]-4'-diethylaminodiphenylamine | 74.3 mg |
| acetone to | 100.0 ml |

A faintly yellowish test paper is obtained which, when dipped into leukocyte-containing urines, turns light to dark blue, according to the leukocyte concentration.

With the other substrates, too, of Examples 1 and 2, as well as with other phosphoric acid derivatives, such as phosphoric acid trimethylamide, phosphoric acid monoethyl ester dimorpholide, phosphoric acid monophenyl ester dimorpholide, ethylphosphonic acid dimorpholide, phenylphosphonic acid bidiethylamide, and phenylphosphonic acid dimorpholide, white to faintly yellowish papers were obtained which, in comparison to analogous test papers without phosphoric acid derivates, were marked by a clearly increased resistance of the impregnated substrates to hydrolysis.

Furthermore, with the aid of the phosphoric acid derivates mentioned in this example, success was achieved in building oxidizing agents of Example 4, along with reducing agents (antioxidants) of Example 6, into a stable preparation.

EXAMPLE 8

Filter paper (for example, Schleicher & Schüll 23 SL) is successively impregnated with the following solutions, and then dried at 60° C. or room temperature.

Solution 1

| | |
|---|---|
| disodium tetraborate decahydrate | 1.91 g |
| distilled water about | 60 ml |

The solution is adjusted with 1M hydrochloric acid to a pH value of 8.0.
distilled water: to 100.0 ml.

Solution 2

Substrate solutions $1 \times 10^{-3}$M in acetone r.g.

The activators of general formula V according to the present invention are added to Solution 2, so that an end-concentration of 2% (w/v) results; 0.5 mmol of activators of general formula VI is dissolved in Solution 1.

The test results with the following esterase or protease substrates are summarized in Table 1:

A: 4-[N-(toluene-4"-sulfonyl)-L-alanyloxy]-4'-dimethylaminodiphenylamine

B: 3-bromo-4-[N-(toluene-4"-sulfonyl)-L-alanyloxy]-4'-dimethylaminodiphenylamine C: 4-[N-(toluene-4"-sulfonyl)-L-alanyloxy]-3'-trifluoromethyl-4'-dimethylaminodiphenylamine D: 4-[N-(toluene-4"-sulfonyl)-L-valyloxy]-4'-dimethylaminodiphenylamine In Table 1, the reaction times are entered that elapse between the dipping of the test strip into a standard solution of 5,000 leukocytes/µl of isotonic salt solution and the first clear color reaction. The reaction times of the corresponding preparations without the additions of activators serve as reference values.

The change of color in the four compounds investigated here takes place from colorless to deep blue.

TABLE 1

| | Activators | Reaction Times for Substrates | | | |
|---|---|---|---|---|---|
| | | A | B | C | D |
| | Comparison Preparation without Activators | 120 s | 230 s | 215 s | 180 s |
| 1. | 1-Hexanol | 70 s | 200 s | 180 s | 100 s |
| 2. | 1-Heptanol | 75 s | 180 s | 180 s | 110 s |
| 3. | 1-Octanol | 75 s | 210 s | 190 s | 90 s |
| 4. | 1-Nonanol | 65 s | 200 s | 170 s | 90 s |
| 5. | 1-Decanol | 35 s | 175 s | 150 s | 80 s |
| 6. | 1-Dodecanol | 50 s | 190 s | 160 s | 120 s |
| 7. | 1-Tetradecanol | 32 s | 140 s | 140 s | 70 s |
| 8. | 1-Pentadecanol | 40 s | 160 s | 145 s | 95 s |
| 9. | 1-Hexadecanol | 45 s | 160 s | 170 s | 90 s |
| 10. | 1-Heptadecanol | 55 s | 150 s | 180 s | 105 s |
| 11. | 1-Octadecanol | 50 s | 180 s | 200 s | 110 s |
| 12. | 1-Nonadecanol | 60 s | 210 s | 200 s | 110 s |
| 13. | 1-Eicosanol | 55 s | 190 s | 210 s | 120 s |
| 14. | 1-Docosanol | 75 s | 180 s | 200 s | 120 s |
| 15. | Cyclohexanol | 90 s | 190 s | 150 s | 120 s |
| 16. | 1-Cyclohexen-3-ol | 110 s | 210 s | 160 s | 150 s |
| 17. | Cycloheptanol | 90 s | 105 s | 180 s | 120 s |
| 18. | Cyclooctanol | 85 s | 205 s | 180 s | 110 s |
| 19. | Cyclononanol | 80 s | 210 s | 150 s | 110 s |
| 20. | Cyclodecanol | 105 s | 200 s | 180 s | 100 s |
| 21. | Cyclododecanol | 100 s | 190 s | 180 s | 100 s |
| 22. | Cycloheptadecanol | 110 s | 205 s | 190 s | 110 s |
| 23. | 9-Cycloheptadecen-1-ol | 55 s | 180 s | 170 s | 110 s |
| 24. | Citronellol | 35 s | 160 s | 150 s | 90 s |
| 25. | Geraniol | 45 s | 190 s | 150 s | 95 s |
| 26. | Nerol | 60 s | 190 s | 160 s | 130 s |
| 27. | Linalool | 75 s | 200 s | 180 s | 110 s |
| 28. | Farnesol | 55 s | 180 s | 160 s | 110 s |
| 29. | Nerolidol | 60 s | 190 s | 190 s | 100 s |
| 30. | (Z)-9-Octadecen-1-ol | 40 s | 160 s | 140 s | 60 s |
| 31. | Phytol | 45 s | 155 s | 150 s | 80 s |
| 32. | 1,5-Pentandiol | 70 s | 230 s | 200 s | 150 s |
| 33. | 1,6-Hexandiol | 70 s | 220 s | 210 s | 150 s |
| 34. | 1,7-Heptandiol | 105 s | 225 s | 200 s | 130 s |
| 35. | 1,8-Octandiol | 90 s | 230 s | 215 s | 100 s |
| 36. | 1,9-Nomandiol | 95 s | 240 s | 220 s | 110 s |
| 37. | 1,10-Decandiol | 110 s | 240 s | 220 s | 160 s |
| 38. | 1,12-Dodecandiol | 110 s | 230 s | 230 s | 180 s |
| 39. | 2-Butyloxyethanol | 80 s | 205 s | 200 s | 100 s |
| 40. | 2-(z-Butyloxyethyloxy)ethanol | 95 s | 200 s | 100 s | 120 s |
| 41. | Tripotassium hexacyanoferrate-III | 110 s | 285 s | 200 s | 180 s |
| 42. | Tetrapotassium hexacyanoferrate-II | 130 s | 200 s | 180 s | 160 s |

TABLE 1-continued

| Activators Comparison Preparation without Activators | Reaction Times for Substrates | | | |
|---|---|---|---|---|
| | A | B | C | D |
| | 120 s | 230 s | 215 s | 180 s |
| 43. Dipotassium tetracyanonickelate | 150 s | 210 s | 210 s | 160 s |
| 44. Trisodium octacyanomolybdate-V | 120 s | 230 s | 200 s | 170 s |
| 45. Disodium pentacyanonitrosyl ferrate-II | 90 s | 175 s | 170 s | 160 s |
| 46. Tripotassium pentacyanonitrosyl manganate-I | 80 s | 160 s | 215 s | 150 s |
| 47. Tripotassium pentacyanonitrosyl chromate-I | 120 s | 200 s | 200 s | 150 s |
| 48. Tripotasium pentacyanonitrosyl cobaltate-I | 100 s | 240 s | 195 s | 190 s |
| 49. Pentapotassium pentacyano nitrosyl vanadate-I | 140 s | 260 s | 200 s | 190 s |

Similar test results are obtained with the other substrates of Examples 1 and 2 and/or leukocyte-containing urines instead of the standard solution of 5,000 leukocytes/$\mu$l of isotonic salt solution.

EXAMPLE 9

Filter paper (for example, Schleicher & Schüll 23 SL) is successively impregnated with the following solutions, and then dried at 60° C. or room temperature.

Solution 1

| disodium tetraborate decahydrate | 1.91 g |
|---|---|
| distilled water about | 60 ml |

The solution is adjusted with 1M hydrochloric acid to pH 8.5.
distilled water: to 100.0 ml.

Solution 2

| 2-methoxy-4-[N—(toluene-4″-sulfonyl)-L-valyloxy]-4′-dimethylaminodiphenylamine | 51.1 mg |
|---|---|
| acetone to | 100.0 ml |

The activators according to the present invention are added individually or as a mixture to Solution 1 and/or Solution 2, according to their solubility, so that with the individual activators of general formulas V and VI, end-concentrations of 2% (w/v) or $5 \times 10^{-3}$M result at any given time.

The reaction times between the dipping of the test strips into a standard solution of 5,000 leukocytes/$\mu$l of isotonic salt solution and the first clear color reaction are entered in Table 2. The reaction time of the preparation without the additions of activators serves as a reference value.

When dipped into leukocyte-containing solutions, the test papers change color from white to deep blue.

TABLE 2

| Activators | Reaction Times |
|---|---|
| Comparison Preparation without Activators | 210 s |
| 1. 1 decanol | 95 s |
| 2. 1-tetradecanol | 90 s |
| 3. disodium pentacyanonitrosyl ferrate-II | 130 s |
| 4. tetrapotassium hexacyanoferrate-II | |

TABLE 2-continued

| Activators | Reaction Times |
|---|---|
| ferrate-II | |
| Activators 1 and 3 | 75 s |
| Activators 1 and 4 | 80 s |
| Activators 2 and 3 | 60 s |
| Activators 2 and 4 | 65 s |

Similar test results are obtained with the other substrates of Examples 1 and 2 and/or leukocyte-containing urines instead of the standard solution of 5,000 leukocytes/$\mu$l of isotonic salt solution.

EXAMPLE 10

A tablet containing

| 4-N—benzoyl-D,L-alanyloxy)-4′-dimethylaminodiphenylamine | 3.0 mg |
|---|---|
| potassium dihydrogen phosphate | 1.5 mg |
| disodium hydrogen phosphate dihydrate | 30.0 mg |
| mannite to | 90.0 mg | is added to 2 ml of a leukocyte-containing urine in a test tube. The urine gradually changes color to light green to deep blue, according to the leukocyte concentration.

After being allowed to stand for 10 minutes at room temperature, the leukocyte concentration is determined visually, with the aid of comparison colors, or photometrically, for example, in 1 cm-microcuvettes at 660 nm.

The sensitivity of the test lies at 390 leukocytes/$\mu$l of urine.

Similar sensitivities (300–1,000 leukocytes/$\mu$l) can be achieved with the other substrates of Examples 1 and 2, and in so doing, the addition of organic solvents, such as, for example, methanol or dimethylformamide, is recommended with difficultly soluble substrates.

With oxidizing agents, wetting agents, antioxidants, stabilizers, and/or activators, comparable effects are also achieved with reagent tablets, as described in Examples 4–9 for test strips.

EXAMPLE 11

Filter paper (for example, Schleicher & Schüll 23 SL) is successively impregnated with the following solutions, and then dried at 60° C.

Solution 1

| disodium tetraborate decahydrate | 1.91 g |
|---|---|
| distilled water about | 30 ml |

The solution is adjusted with 0.1N hydrochloric acid to a pH value of 8.0.
distilled water: to 100.0 ml.

Solution 2

| 4-[N—(toluene-4″-sulfonyl)-L-phenylalanyloxy]-4′-dimethylaminodiphenylamine | 51.5 mg |
|---|---|
| acetone to | 100.0 ml |

A colorless test paper is obtained which, when dipped into aqueous solutions containing the proteolytic enzyme chymotrypsin, turns blue. Even concentrations of 0.005 U chymotrypsin per ml can be detected in this way in about 2-4 minutes.

(The enzyme activity indicated was determined with N-acetyl-L-tyrosin-ethyl ester as substrate 25° C., pH 7.0, and λ=237 nm.

Chymotrypsin or other proteolytic enzymes, such as, for example, elastase or trypsin, can be determined with the other substrates, too, of Examples 1 and 2, according to the amino acid or peptide radical, in purely aqueous solutions, or also, for example, in body fluids, such as, for example, whole blood, serum, liquor, pancreatic secretion, and aqueous stool extracts.

It will be understood that the specification and examples are illustrative but not limitative of the present invention and that other embodiments within the spirit and scope of the invention will suggest themselves to those skilled in the art.

What is claimed is:

1. Composition for detection of proteolytic enzymes comprising a buffering substance and, as a chromogen, an effective amount for use as a chromogen for the detection of proteolytic enzymes of at least one leuko-indoaniline amino acid ester or a peptide ester compound of the formula

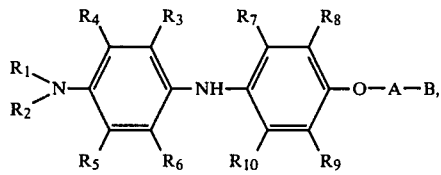

wherein
$R_1$ and $R_2$, which can be identical or different, each is hydrogen, a lower alkyl or a hydroxy-lower alkyl group; or
$R_1$ and $R_2$ together are an alkylene or alkylene-oxy-alkylene chain;
$R_3$, $R_4$, $R_5$ and $R_6$, which can be identical or different, each is hydrogen or halogen, lower alkyl, lower haloalkyl, lower alkoxy, an aralkoxy, a hydroxy, or a nitro group;
$R_7$, $R_8$, $R_9$ and $R_{10}$, which can be identical or different, each is hydrogen or halogen; a substituted or unsubstituted group selected from the group consisting of a lower alkyl, lower haloalkyl, lower alkoxy, an aralkoxy, a lower acylamino, an acylalkenyl, a hydroxy, a lower alkylmercapto, a lower alkyl sulfonyl, a carboxy, or a carbonyl group a group wherein two adjacent substituents form a saturated or unsaturated hydrocarbon chain, or a saturated or unsaturated hydrocarbon chain containing a nitrogen atom in the chain;
A is an amino acid or a peptide radical; and
B is an amine protective group.

2. Composition as claimed in claim 1 also comprising adjuvants and activators.

3. Composition as claimed in claim 2 wherein said adjuvants are selected from the group consisting of wetting agents, oxidizing agents, antioxidants, stabilizers, film-formers and admixed galenic materials.

4. Composition as claimed in claim 1 wherein said chromogen is 4-[N-(toluene-4"-sulfonyl)-L-alanyloxy]-4'-dimethylamino-diphenylamine.

5. Composition as claimed in claim 1 wherein said chromogen is 4-[N-(toluene-4"-sulfonyl)-L-alanyloxy]-2'-bromo-4'-dimethylamino-diphenylamine.

6. Composition as claimed in claim 1 wherein said chromogen is 3-methoxy-4-[N-(toluene-4"-sulfonyl)-L-alanyloxy]-4'-dimethylamino-diphenylamine.

7. Composition as claimed in claim 1 wherein said chromogen is 4-[N-(toluene-4"-sulfonyl)-L-valyloxy]-4'-dimethylamino-diphenylamine.

8. Composition as claimed in claim 1 also comprising, as an adjuvant, a phosphoric or phosphonic acid amide of the formula

wherein
$R_{11}$ is dialkylamino, an alkoxy, an aryloxy, an alkyl or an aryl group or an N-morpholine radical; and
$R_{12}$ and $R_{13}$ each represent a dialkylamino group or an N-morpholine radical.

9. Composition as claimed in claim 1 also comprising an alcohol of the formula $$R_{14}-K-OH \qquad (V)$$

wherein
$R_{14}$ is hydrogen, a hydroxy or a lower alkoxy group; and
K is a hydrocarbon radical or a metal complex of the formula $$D_m[M(CN)_n(NO)_p] \qquad (VI)$$

wherein
D is an alkali metal ion;
M is a heavy metal ion;
m is 2, 3, 4 or 5;
n is 4, 5, 6, 7 or 8; and
p is 0 or 1.

10. Composition as claimed in claim 1 wherein an absorbent carrier is impregnated with said chromogen and buffer material.

11. Composition as claimed in claim 1 in reagent tablet form.

12. Method of detecting proteolytic enzymes in a sample, which method comprises contacting a buffering substance and at least one chromogen selected from the leuko-indoaniline amino acid and peptide ester compounds under conditions wherein the enzymes will split the esters into leuko-indoaniline compounds which are deep blue colored, of the formula

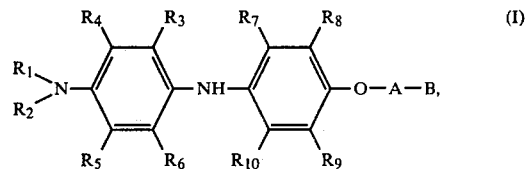

wherein
$R_1$ and $R_2$, which can be identical or different, each is hydrogen, a lower alkyl or a hydroxy-lower alkyl group; or
$R_1$ and $R_2$ together are an alkylene or alkylene-oxy-alkylene chain;
$R_3$, $R_4$, $R_5$ and $R_6$, which can be identical or different, each is hydrogen or halogen, lower alkyl, lower haloalkyl, lower alkoxy, an aralkoxy, a hydroxy, or a nitro group;

$R_7$, $R_8$, $R_9$ and $R_{10}$, which can be identical or different, each is hydrogen or halogen; a substituted or unsubstituted group selected from the group consisting of a lower alkyl, lower haloalkyl, lower alkoxy, an aralkoxy, a lower acylamino, an acylalkenyl, a hydroxy, a lower alkylmercapto, a lower alkyl sulfonyl, a carboxy, or a carbonyl group a group wherein two adjacent substituents form a saturated or unsaturated hydrocarbon chain, or a saturated or unsaturated hydrocarbon chain containing a nitrogen atom in the chain;

A is an amino acid or a peptide radical; and

B is an amine protective group and thereafter measuring the color intensity of the indoaniline formed.

13. The method of claim 12 wherein the oxidizing step comprises exposing the reaction mixture to air.

* * * * *